(12) United States Patent
Van Schie

(10) Patent No.: US 8,772,303 B2
(45) Date of Patent: Jul. 8, 2014

(54) PHARMACEUTICAL FORMULATION

(75) Inventor: Dirk Marinus Johannes Van Schie, Essex (GB)

(73) Assignee: Glaxo Group Limited, Brentford, Middlesex (GB)

( * ) Notice: Subject to any disclaimer, the term of this patent is extended or adjusted under 35 U.S.C. 154(b) by 636 days.

(21) Appl. No.: 12/478,934

(22) Filed: Jun. 5, 2009

(65) Prior Publication Data

US 2009/0306113 A1    Dec. 10, 2009

Related U.S. Application Data

(63) Continuation of application No. 10/570,335, filed as application No. PCT/EP2004/009726 on Aug. 31, 2004, now abandoned.

(51) Int. Cl.
*A61K 31/513* (2006.01)

(52) U.S. Cl.
USPC .................. 514/274; 514/258.1; 544/253

(58) Field of Classification Search
USPC ................. 514/258.1, 274; 544/253
See application file for complete search history.

(56) References Cited

U.S. PATENT DOCUMENTS

| | | | |
|---|---|---|---|
| 4,971,805 A | 11/1990 | Kitanishi et al. | |
| 5,576,025 A | 11/1996 | Akiyama et al. | |
| 5,614,220 A | 3/1997 | Hirakawa et al. | |
| 5,725,880 A | 3/1998 | Hirakawa et al. | |
| 6,268,385 B1 | 7/2001 | Whittle et al. | |
| 6,296,876 B1 | 10/2001 | Odidi et al. | 424/480 |
| 6,328,994 B1 * | 12/2001 | Shimizu et al. | 424/489 |
| 6,455,052 B1 | 9/2002 | Marcussen et al. | 424/234.1 |
| 2002/0068088 A1 | 6/2002 | Gruber | |
| 2002/0103213 A1 | 8/2002 | Hickey et al. | 514/269 |
| 2004/0089753 A1 | 5/2004 | Holland et al. | 241/21 |

FOREIGN PATENT DOCUMENTS

| | | |
|---|---|---|
| DE | 3619570 C1 | 10/1987 |
| DE | 3943242 | 6/1990 |
| EP | 0754452 A2 | 7/1996 |
| EP | 1405621 A1 | 4/2004 |
| RU | 2203671 C1 | 5/2003 |
| WO | WO 97/46224 | 12/1997 |
| WO | WO 98/06385 | 2/1998 |
| WO | WO 00/28989 | 5/2000 |
| WO | WO 01/60805 | 8/2001 |
| WO | WO 01/76392 | 10/2001 |

OTHER PUBLICATIONS

Granaro et al., Gastrointestinal dissolution and absorption of drugs, Drug Bioavailability estimation of Solubility, Permeability, Absorption and Bioavailability, 2003, Wiley, pp. 189-214.*
Blackie Josie, et al. "The identification of clinical candidate SB-480848: A potent inhibitor of lipoprotein-associated phospholipase A2." Bioorganic and Medicinal Chemistry Letters, vol. 13 mo. 6, Mar. 24, 2003, pp. 1067-1070.

(Continued)

*Primary Examiner* — Savitha Rao
(74) *Attorney, Agent, or Firm* — Loretta J. Sauermelch; Alan X. Scrivner

(57) ABSTRACT

The present invention provides enteric polymer coated tablet formulations for oral administration which comprise a phospholipase A2 enzyme Lipoprotein Associated Phospholipase A2 (Lp-PLA2) inhibitor, processes for preparing such formulations and their use in therapy, in particular the treatment of atherosclerosis.

25 Claims, 1 Drawing Sheet

(56) References Cited

OTHER PUBLICATIONS

Arthur J. Kibbe "Handbook of Pharmaceutical Excipients, Third Edition" 2000, American Pharmaceutical Association Washington D.C. p. 401-406.
DE 3619570 C1 Machine Translation—PatBase.
DE 3619570 C1 Machine Translation—Google.
DE 3619570 C1 Abstract—Chemical Abstracts.
DE 3619570 C1 abstract—Derwent.
RU 2203671 C1 Machine Translation—Mine Soft.
RU 2203671 C1 abstract—Chemical Abstracts.
RU 2203671 C1 abstract—Derwent.
Kondo, et al.; Improved Oral Absorption of a Poorly Water-Soluble Drug, HO-221, by Wet-Bead Milling Producing Particles in Submicron Region; Chem Parm. Bull. vol. 41(4), p. 737-740 (1993).
DE 3619570 Espacenet abstract.
RU 2203671 Espacenet abstract.

* cited by examiner

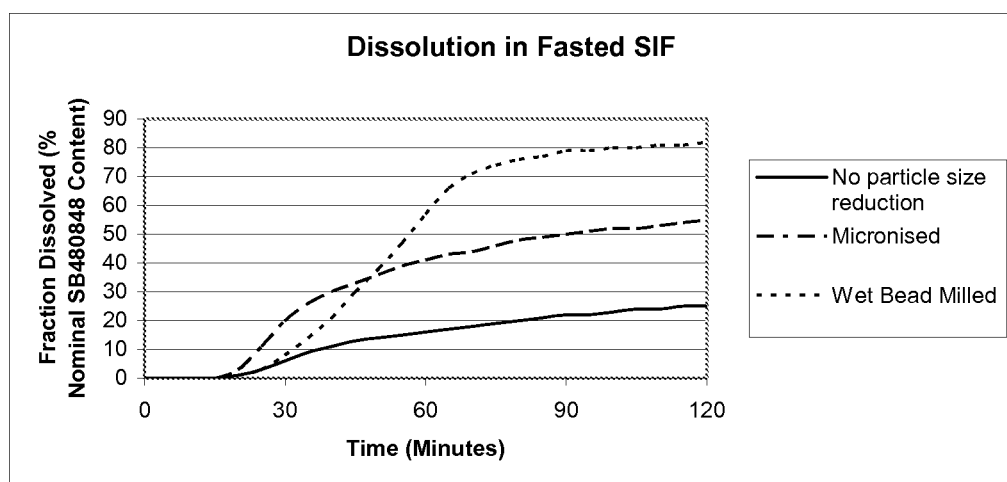

PHARMACEUTICAL FORMULATION

This application is a continuation application derived from U.S. Ser. No. 10/570,335 filed 1 Mar. 2006 now abandoned which is a 371 of Application No. PCT/EP2004/009726 filed 31 Aug. 2004.

This invention relates to tablet formulations for oral administration which comprise a phospholipase A2 enzyme Lipoprotein Associated Phospholipase A2 (Lp-PLA2) inhibitor, processes for preparing such formulations and their use in therapy, in particular the treatment of atherosclerosis.

WO 01/60805 (SmithKline Beecham plc), discloses a novel class of pyrimidinone compounds, inter alia those substituted at N1 and containing a sulphur atom.

The pyrimidinone compounds described in WO 01/60805 are inhibitors of the enzyme lipoprotein associated phospholipase $A_2$ (Lp-PLA$_2$) and as such are expected to be of use in therapy, in particular in the primary and secondary prevention of acute coronary events, for instance those caused by atherosclerosis, including peripheral vascular atherosclerosis and cerebrovascular atherosclerosis. The compounds of Formula I described in the present invention are a subset of those described in WO 01/60805.

Following administration of a compound of formula I during phase I clinical trials odour related adverse events were observed. These included abnormal smelling faeces, urine, sweat and hair. We now propose that this adverse event was caused by degradation of the compounds in the acidic environment of the stomach to produce a degradation product containing a free thiol group. We further believe that this breakdown is less likely to occur in the less acidic intestinal environment. The present invention addresses this problem by providing compounds of formula I in a tablet formulation cased with an enteric polymer coating. The term "enteric polymer" is a term of the art referring to a polymer which is preferentially soluble in the less acid environment of the intestine relative to the more acid environment of the stomach.

Accordingly, in a first aspect the instant invention provides a pharmaceutical formulation comprising a core which includes a pharmaceutically active ingredient which is a compound of formula (I):

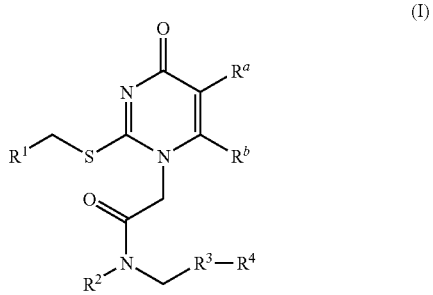

wherein:
$R^a$ and $R^b$ together are $(CH_2)_n$ where n is 3 or 4, to form, with the pyrimidine ring carbon atoms to which they are attached, a fused 5- or 6-membered carbocyclic ring; and
$R^1$ is phenyl optionally substituted by halogen;
$R^2$ is $C_{(1-3)}$alkyl substituted by $NR^5R^6$;
$R^3$ and $R^4$ form a 4-(4-trifluoromethylphenyl)phenyl moiety; and
$R^5$ and $R^6$ which may be the same or different is each selected from hydrogen, or $C_{(1-6)}$alkyl;

And a casing which comprises an enteric polymer.

Preferably, Ra and Rb together with the pyrimidine ring carbon atoms to which they are attached form a fused 5 membered carbocyclic ring.

Preferably, R1 is substituted by a single halogen in the para position. Particularly preferably said halogen is fluoro.

Preferably R5 and R6 are both C(1-6) alkyl, particularly preferably they are both ethyl.

In a preferred embodiment, the pharmaceutically active ingredient is 1-(N-(2-(Diethylamino)ethyl)-N-(4-(4-trifluoromethylphenyl)benzyl)aminocarbonylmethyl)-2-(4-fluorobenzyl)thio-5,6-trimethylenepyrimidin-4-one.

The active material in the core may be present in any conventional form; it may be present in a micronised form; a milled form, in particular a wet bead milled form; or in a solubilised form. In addition to active materials the core may contain additives conventional to the art of compressed tablets. Appropriate additives in such a tablet may comprise diluents (also known to the person skilled in the art as fillers) such as microcrystalline cellulose, mannitol, anhydrous lactose, lactose monohydrate, calcium carbonate, magnesium carbonate, dicalcium phosphate or mixtures thereof; binders such as hydroxypropylmethylcellulose, hydroxypropyl-cellulose, polyvinylpyrrolidone, pre-gelatinised starch or gum acacia or mixtures thereof; disintegrants such as microcrystalline cellulose (fulfilling both diluent and disintegrant functions) cross-linked polyvinylpyrrolidone, sodium starch glycollate, croscarmellose sodium or mixtures thereof; lubricants, such as magnesium stearate or stearic acid, glidants or flow aids, such as colloidal silica, talc or starch, and stabilisers such as poloxamer, desiccating amorphous silica, colouring agents, flavours etc. Preferably the tablet comprises lactose as diluent. When a binder is present, it is preferably hydroxypropylmethylcellulose. Preferably, the tablet comprises magnesium stearate as lubricant. Preferably the tablet comprises croscarmellose sodium as disintegrant. Preferably, the tablet comprises microcrystalline cellulose as diluent.

The diluent may be present in a range of 10-80% by weight of the core. The lubricant may be present in a range of 0.25-2% by weight of the core. The disintegrant may be present in a range of 1-10% by weight of the core. Microcrystalline cellulose, if present, may be present in a range of 10-80% by weight of the core.

The active ingredient preferably comprises between 10 and 50% of the weight of the core, more preferably between 15 and 40% of the weight of the core. The core may contain any therapeutically suitable dosage level of the active ingredient, but preferably contains up to 200 mg as free base of the active ingredient. Particularly preferably, the core contains 20, 30, 40, 50, 60, 80, 100, 120 or 160 mg as free base of the active ingredient.

The core may be made from a compacted mixture of its components. The components may be directly compressed, or may be granulated before compression. Such granules may be formed by a conventional granulating process as known in the art. In another aspect the core may be made by a process comprising spray-drying of a wet bead milled suspension of active. In an alternative embodiment, the granules may be individually coated with an enteric casing, and then enclosed in a standard capsule casing.

The core is surrounded by a casing which comprises an enteric polymer. Examples of enteric polymers are cellulose acetate phthalate, cellulose acetate succinate, methylcellulose phthalate, ethylhydroxycellulose phthalate, polyvinylacetate phthalate, polyvinylbutyrate acetate, vinyl acetate-maleic anhydride copolymer, styrene-maleic mono-ester copolymer, methyl acrylate-methacrylic acid copolymer or methacrylate-methacrylic acid-octyl acrylate copolymer. These may be used either alone or in combination, or together with other polymers than those mentioned above. The casing may also include insoluble substances which are neither decomposed nor solubilised in living bodies, such as alkyl cellulose derivatives such as ethyl cellulose, crosslinked polymers such as styrene-divinylbenzene copolymer, polysaccharides having hydroxyl groups such as dextran, cellulose derivatives which are treated with bifunctional crosslinking agents such as epichlorohydrin, dichlorohydrin or 1,2-, 3,4-diepoxybutane. The casing may also include starch and/or dextrin.

Preferred enteric coating materials are the commercially available Eudragit® enteric polymers such as Eudragit® L, Eudragit® S and Eudragit® NE used alone or with a plasticiser. Such coatings are normally applied using a liquid medium, and the nature of the plasticiser depends upon whether the medium is aqueous or non-aqueous. Plasticisers for use with aqueous medium include propylene glycol, triethyl citrate, acetyl triethyl citrate or Citroflex® or Citroflex® A2. Non-aqueous plasticisers include these, and also diethyl and dibutyl phthalate and dibutyl sebacate. A preferred plasticiser is Triethyl citrate. The quantity of plasticiser included will be apparent to those skilled in the art.

The casing may also include an anti-tack agent such as talc, silica or glyceryl monostearate. Preferably the anti-tack agent is glyceryl monostearate. Typically, the casing may include around 5-25 wt % Plasticiser and up to around 50 wt. % of anti tack agent, preferably 1-10 wt. % of anti-tack agent.

If desired, a surfactant may be included to aid with forming an aqueous suspension of the polymer. Many examples of possible surfactants are known to the person skilled in the art. Preferred examples of surfactants are polysorbate 80, polysorbate 20, or sodium lauryl sulphate. If present, a surfactant may form 0.1-10% of the casing, preferably 0.2-5% and particularly preferably 0.5-2%

In one embodiment, there is a seal coat included between the core and the enteric coating. A seal coat is a coating material which can be used to protect the enteric casing from possible chemical attack by any alkaline ingredients in the core. The seal coat may also provide a smoother surface, thereby allowing easier attachment of the enteric casing. A person skilled in the art would be aware of suitable coatings. Preferably the seal coat is made of an Opadry coating, particularly preferably it is Opadry White, and more particularly preferably it is Opadry White OY-S-28876.

The present invention also provides a pharmaceutical formulation as described herein for use as an active therapeutic substance. Preferably, the formulation is for use in the treatment of atherosclerosis.

The invention will now be described by way of example only.

EXAMPLE 1

Tablets comprise varying amounts of —(N-(2-(Diethylamino)ethyl)-N-(4-(4-trifluoromethylphenyl)benzyl)aminocarbonylmethyl)-2-(4-fluorobenzyl)thio-5,6-trimethylenepyrimidin-4-one (called "active ingredient" in this example) as the free base (see Table 1).

Lactose monohydrate, microcrystalline cellulose, the active ingredient, the hydroxypropyl methyl cellulose and a portion of the croscarmellose sodium (in accordance with the formula) were screened into a 10 Liter Fielder high-shear blender (any suitable high shear blender could be used) and blended for 5 minutes at 300 rpm with the chopper off. The mixture was then granulated by the addition of about 900 ml water whilst continuing to blend using both the impeller (300 rpm) and the chopper (speed II). The granules were dried in a Glatt 3/5 fluid bed drier, screened by Comil into a Pharmatec 10 Liter bin blender and then blended with any lactose anhydrous given in the formula plus the remainder of the croscarmellose sodium over 15 minutes at 17 rpm. Magnesium stearate was screened into the blender and the mixing process continued for a further 2 minutes at 17 rpm. The lubricated mix was compressed using a Riva Piccola rotary tablet press fitted with 10.5 mm round normal concave punches (any suitable tablet press could be used). The seal-coat, and subsequently the enteric coat, are applied by spraying of an aqueous suspension of the coat ingredients in a Manesty XL coater using parameters for the coating process as recommended by the manufacturers of the coating polymers (any suitable coater could be used).

This technique can be carried out as described above using micronised active to produce tablets containing varying amounts of micronised active as the free base.

EXAMPLE 2

Tablets comprise varying amounts of —(N-(2-(Diethylamino)ethyl)-N-(4-(4-trifluoromethylphenyl)benzyl)aminocarbonylmethyl)-2-(4-fluorobenzyl)thio-5,6-trimethylenepyrimidin-4-one (called "active ingredient" in this example) as the free base (see Table 2).

A suspension of the active ingredient, hydroxypropyl methyl cellulose, poloxamer 188 and mannitol in purified water was prepared using a paddle stirrer (any suitable stirrer or homogeniser could be used). The suspension was then passed through a Drais Cosmo wet bead mill containing yttrium/zirconium beads (any suitable wet bead mill could be used) until the desired particle size was achieved. The milled suspension was then spray dried using a Niro Mobile Minor spray drier (any suitable spray drier could be used). The spray dried powder was then added into a Pharmatec 5 Liter bin blender and then blended with microcrystalline cellulose and croscarmellose sodium over 10 minutes at 17 rpm. Magnesium stearate was screened into the blender and the mixing process continued for a further 1 minute at 17 rpm. The lubricated mix was compressed using a Korsch EKO single punch tablet press fitted with 9 mm round normal concave punches (any suitable tablet press could be used). The seal-coat, and subsequently the enteric coat, are applied by spraying of an aqueous suspension of the coat ingredients in a Manesty XL coater using parameters for the coating process as recommended by the manufacturers of the coating polymers (again, any suitable coater could be used).

EXAMPLE 3

Tablets comprise 60 mg of 1-(N-(2-(Diethylamino)ethyl)-N-(4-(4-trifluoromethylphenyl)benzyl)aminocarbonylmethyl)-2-(4-fluorobenzyl)thio-5,6-trimethylenepyrimidin-4-one (called "active ingredient" in this example) as free base (see Table 3).

Lactose anhydrous, microcrystalline cellulose, croscarmellose sodium and the active ingredient were screened into a blender and blended for 15 minutes at 30 rpm. Magnesium stearate was screened into the blender and the mixing process continued for a further 2 minutes at 18 rpm. The lubricated mix was compressed on a rotary tablet press fitted with 9.5 mm round normal concave punches (any suitable tablet press could be used). The enteric coat was applied by spraying of an aqueous suspension of the coat ingredients in a coater, using parameters for the coating process as recommended by the manufacturers of the coating polymers (any suitable coater could be used).

COMPARATIVE EXAMPLE 4

Tablets comprise varying amounts of —(N-(2-(Diethylamino)ethyl)-N-(4-(4-trifluoromethylphenyl)benzyl)aminocarbonylmethyl)-2-(4-fluorobenzyl)thio-5,6-trimethylenepyrimidin-4-one (called "active ingredient" in this example) as Hydrochloride salt (see Table 4).

Lactose monohydrate, microcrystalline cellulose, the active ingredient, the hydroxypropyl methyl cellulose and half of the croscarmellose sodium were screened into a 10 Liter Fielder high-shear blender (any suitable high shear blender could be used) and blended for 5 minutes at 300 rpm with the chopper off. The mixture was then granulated by the addition of about 750 ml water whilst continuing to blend. The granules were dried in a Glatt 3/5 fluid bed drier, screened by Comil into a Pharmatec 5 Liter bin blender and then blended with any lactose anhydrous given in the formula plus the remainder of the croscarmellose sodium over 5 minutes at 20 rpm. Magnesium stearate was screened into the blender and the mixing process continued for a further 1 minute at 10 rpm. The lubricated mix was compressed using a Riva Piccola rotary tablet press fitted with 9.5 mm round normal concave punches (any suitable tablet press could be used). The seal-coat, and subsequently the enteric coat, are applied by spraying of an aqueous suspension of the coat ingredients in a Manesty 10 coater using parameters for the coating process as recommended by the manufacturers of the coating polymers (again, any suitable coater could be used).

TABLE 2

| Component | Quantity (mg/tablet) | Function |
|---|---|---|
| Tablet Core: | | |
| Active ingredient | 80.0 | Active |
| Hypromellose | 8.0 | Stabiliser |
| Mannitol | 40.0 | Dispersant |
| Poloxamer 188 | 16.0 | Stabiliser |
| Microcrystalline Cellulose | 91.0 | Diluent |
| Croscarmellose Sodium | 12.5 | Disintegrant |
| Magnesium Stearate | 2.5 | Lubricant |
| Purified Water [1] | q.s. | Granulating Fluid |
| Nitrogen [2] | q.s. | Processing Aid |
| Core Weight | 250.0 | — |
| Seal Coat | | |
| Opadry OY-S-28876 | 5.0 | Seal Coat |
| Purified Water [1] | q.s. | Coating Fluid |
| Enteric Coat: | | |
| Methacrylic Acid Copolymer Dispersion 30% [3] | 16.7 | Enteric Polymer |
| Triethyl Citrate | 2.5 | Plasticizer |
| Glyceryl Monostearate | 0.5 | Anti-Tack Agent |
| Polysorbate 80 | 0.2 | Solubilizer |
| Purified Water [1] | q.s. | Coating Fluid |
| Total | 274.9 | — |

[1] Water is removed during processing.
[2] Nitrogen is used as a processing aid during spray drying.
[3] Eudragit ® L30 D-55. The quantity listed represents the 30% solids content in Eudragit ® L30 D-55. It is calculated to give approximately 6.5 mg/cm$^2$ dry polymer per tablet surface area.

TABLE 1

| | Quantity (mg/tablet) | | | |
|---|---|---|---|---|
| Component | 80 mg | 120 mg | 160 mg | Function |
| Tablet Core: | | | | |
| Active ingredient | 80.0 | 120.0 | 160.0 | Active |
| Lactose Monohydrate | 61.9 | 92.9 | 123.8 | Diluent |
| Microcrystalline Cellulose | 40.1 | 60.1 | 80.2 | Diluent |
| Hypromellose | 10.0 | 15.0 | 20.0 | Binder |
| Croscarmellose Sodium | 9.0 | 10.5 | 12.0 | Disintegrant |
| Lactose Anhydrous | 195.0 | 97.5 | — | Diluent |
| Magnesium Stearate | 4.0 | 4.0 | 4.0 | Lubricant |
| Purified Water [1] | q.s. | q.s. | q.s. | Granulating Fluid |
| Core Weight | 400.0 | 400.0 | 400.0 | — |
| Seal-Coat | | | | |
| Opadry OY-S-28876 | 8.0 | 8.0 | 8.0 | Seal Coat |
| Purified Water [1] | q.s. | q.s. | q.s. | Coating Fluid |
| Enteric Coat: | | | | |
| Methacrylic Acid Copolymer Dispersion 30% [2] | 20.5 | 20.5 | 20.5 | Enteric Polymer |
| Triethyl Citrate | 3.1 | 3.1 | 3.1 | Plasticizer |
| Glyceryl Monostearate | 0.6 | 0.6 | 0.6 | Anti-Tack Agent |
| Polysorbate 80 | 0.25 | 0.25 | 0.25 | Solubilizer |
| Purified Water [1] | q.s. | q.s. | q.s. | Coating Fluid |
| Total | 432.5 | 432.5 | 432.5 | — |

[1] Water is removed during processing
[2] Eudragit ® L30 D-55. The quantity listed represents the 30% solids content in Eudragit ® L30 D-55. It is calculated to give approximately 6.5 mg/cm$^2$ dry polymer per tablet surface area.

TABLE 3

| Component | Quantity (mg/tablet) | Function |
|---|---|---|
| Tablet Core: | | |
| Active ingredient | 60.00 | Active ingredient |
| Anhydrous lactose | 124.80 | Diluent |
| Microcrystalline cellulose | 104.00 | Diluent |
| Croscarmellose sodium | 9.00 | Disintegrant |
| Magnesium stearate | 2.20 | Lubricant |
| Purified water[1] | q.s. | Granulating fluid |
| Core Weight | 300.0 | — |
| Enteric Coat: | | |
| Methacrylic acid copolymer dispersion[2] | 26.8 | Enteric Polymer |
| Triethyl Citrate | 3.8 | Plasticizer |
| Glycerol Monostearate | 0.8 | Anti-Tack Agent |
| Polysorbate 80 | 0.3 | Solubilizer |
| Purified Water[1] | q.s. | Coating Fluid |
| Coated Tablet Weight | 331.7 | — |

[1]Water is removed during processing.
[2]Eudragit ® L30 D-55. The quantity listed represents the 30% solids content in Eudragit ® L30 D-55. It is calculated to give approximately 10 mg/cm² dry polymer per tablet surface area.

TABLE 4

| Component | Amount of component present in 5 different dosage strengths | | | | | Function |
|---|---|---|---|---|---|---|
| Tablet Core: | | | | | | |
| Active ingredient | 21.3[1] | 42.5[1] | 63.8[1] | 85.1[1] | 106.4[1] | Active |
| Lactose Monohydrate | 36.1 | 72.2 | 108.3 | 144.5 | 106.6 | Diluent |
| Anhydrous Lactose | 159.4 | 86.3 | 13.2 | — | — | Diluent |
| Hydroxypropyl methyl cellulose | — | — | — | — | 15.0 | Binder |
| Microcrystalline Cellulose | 74.6 | 89.3 | 103.9 | 58.6 | 60.0 | Diluent |
| Croscarmellose Sodium | 5.6 | 6.7 | 7.8 | 8.9 | 9.0 | Disintegrant |
| Magnesium Stearate | 3.0 | 3.0 | 3.0 | 3.0 | 3.0 | Lubricant |
| Purified Water[2] | q.s. | q.s. | q.s. | q.s. | q.s. | Granulating Fluid |
| Core Weight | 300.0 | 300.0 | 300.0 | 300.0 | 300.00 | |
| Seal Coat: | | | | | | |
| Opadry White OY-S-28876 | 6.0 | 6.0 | 6.0 | 6.0 | 6.0 | Seal Coat |
| Purified Water[2] | q.s. | q.s. | q.s. | q.s. | q.s. | Coating Fluid |
| Enteric Coat: | | | | | | |
| Methacrylic Acid Copolymer Dispersion[3] | 26.8 | 26.8 | 26.8 | 26.8 | 26.8 | Enteric Polymer |
| Triethyl Citrate | 3.8 | 3.8 | 3.8 | 3.8 | 3.8 | Plasticizer |
| Glyceryl Monostearate | 0.8 | 0.8 | 0.8 | 0.8 | 0.8 | Anti-Tack Agent |
| Polysorbate 80 | 0.3 | 0.3 | 0.3 | 0.3 | 0.3 | Solubilizer |
| Purified Water[2] | q.s. | q.s. | q.s. | q.s. | q.s. | Coating Fluid |
| Coated Tablet Weight | 337.7 | 337.7 | 337.7 | 337.7 | 337.7 | |

Notes:
[1]Equivalent to 20, 40, 60, 80 and 100 mg respectively of active
[2]Water is removed during processing
[3]Eudragit ® L30 D-55. The quantity listed represents the 30% solids content in Eudragit ® L30 D-55. It is calculated to give approximately 10 mg/cm² dry polymer per tablet surface area.

EXAMPLE 5

Measurement of a Substituted Uracil in Simulated Gastric Fluid and Simulated Intestinal Fluid Compounds of Formula (I) hydrolyse, particularly under conditions where pH corresponds to that typically prevailing in the human stomach, to form a thiol and a uracil in a 1:1 stoichiometric ratio. The thiol has a smell characteristic of compounds of its class, the intensity of the smell increasing with the concentration of the thiol. Thus the concentration of the uracil is a surrogate marker for the intensity of the smell.

To simulate in vitro the effect of enteric-coating on the propensity of 1-(N-(2-(Diethylamino)ethyl)-N-(4-(4-trifluoromethylphenyl)benzyl)aminocarbonylmethyl)-2-(4-fluorobenzyl)thio-5,6-trimethylenepyrimidin-4-one as the free base (called "active" in this example) to give rise to abnormal smells in vivo, a two-armed study was performed. In both arms, 60 mg of active was immersed in 250 mL simulated gastric fluid held at 37° C. and stirred at 50 rpm in a USP2 dissolution apparatus. In one arm, the active was present as an enteric-coated tablet. In the other arm, active was present as the unformulated drug substance, which is chemically equivalent to a tablet lacking an enteric coat.

The uracil produced by the active is N-[2-(diethylamino)ethyl]-2-(2,4-dioxo-2,3,4,5,6,7-hexahydro-1H-cyclopenta[d]pyrimidin-1-yl)-N-{[4'-(trifluoromethyl)-4-biphenylyl]methyl}acetamide, as shown in Formula (II):

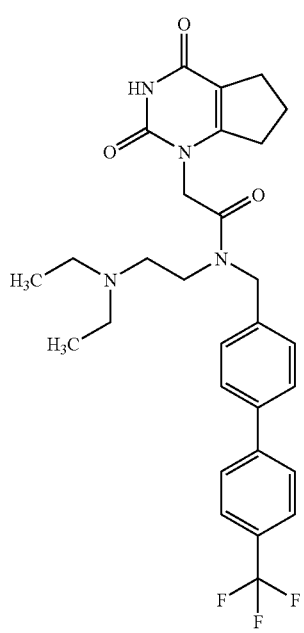

(II)

In both arms, the level of formula (II) in solution was monitored over time, by withdrawing a small sample of the fluid and comparing its LC-MS response to that of a matrix-matched external standard (i.e. synthetic formula (II)).

TABLE 5

| Time (Minutes) | Levels of Formula (II) in simulated gastric fluid (ng/mL) | |
|---|---|---|
| | Enteric coated tablet | Unformulated drug |
| 0 | <QL[1] | 6.27 × 10³ |
| 5 | <QL[1] | 6.57 × 10³ |
| 10 | <QL[1] | 7.18 × 10³ |
| 15 | <QL[1] | 7.97 × 10³ |
| 30 | <QL[1] | 9.27 × 10³ |
| 45 | <QL[1] | 11.45 × 10³ |
| 60 | 1.77 | 13.11 × 10³ |
| 120 | 3.01 | 18.94 × 10³ |
| 240 | 7.09 | 25.25 × 10³ |
| 480 | 12.6 | 62.91 × 10³ |
| 1440 | 14.2 | 135.6 × 10³ |

[1]QL = the concentration below which formula (II) cannot be precisely quantified (which was estimated experimentally to be 1.71 ng/mL).

The results tabulated above clearly show that the enteric coat reduces by 4 orders of magnitude the level of formula (II) (and, by stoichiometry, thiol) formed by active under conditions which are typical of the human stomach. By extension, the data support the hypothesis that enteric-coating an active tablet will reduce, or eliminate, the abnormal smell which would otherwise be produced by the active in vivo.

By its nature, the enteric coat will be destroyed under conditions whose pH correspond to that prevailing in the human intestine.

To simulate in vitro the propensity of active tablets to give rise to abnormal smells in the human intestine, active equivalent to 80 mg was immersed in 250 mL simulated intestinal fluid (corresponding to the fasted state in humans) held at 37° C. and stirred at 50 rpm in a USP2 dissolution apparatus. This is chemically equivalent to a tablet whose enteric coat has been destroyed and whose core has subsequently disintegrated.

The level of formula (II) in solution was monitored over time, by withdrawing a small sample of the fluid and comparing its LC-MS response to that of a matrix-matched external standard (i.e. synthetic formula (II)).

TABLE 6

| Time (Minutes) | Levels of formula (II) in simulated intestinal fluid (ng/mL) Unformulated drug |
|---|---|
| 0 | <QL |
| 5 | <QL |
| 10 | <QL |
| 15 | <QL |
| 30 | <QL |
| 45 | <QL |
| 60 | <QL |
| 120 | <QL |
| 240 | <QL |
| 480 | 2.99 |
| 1440 | 8.58 |

QL: the concentration below which formula (II) cannot be precisely quantified (which was estimated experimentally to be 1.71 ng/mL).

The results tabulated above clearly show that, in contrast to its behaviour in simulated gastric fluid, active has a low propensity to form formula (II) in simulated intestinal fluid and therefore, as argued for simulated gastric fluid, is likely to have a low propensity to produce an abnormal smell in the human intestine.

EXAMPLE 6

Results of a study comparing adverse events seen with enterically coated and non-enterically coated tablets.

A double-blind, 4-session, cross-over, placebo controlled, randomized, repeat dose, relative bioavailability study, was conducted using 60 mg of 1-(N-(2-(Diethylamino)ethyl)-N-(4-(4-trifluoromethylphenyl)benzyl)aminocarbonylmethyl)-2-(4-fluorobenzyl)thio-5,6-trimethylenepyrimidin-4-one. The trial looked at odor-related adverse events seen with standard free base formulation compared to enteric coated free base and enteric coated hydrochloride salt. The number of subjects exposed to the hydrochloride salt, enteric coated formulation was comparable to that exposed to free base.

TABLE 7

| | Free base, non-enteric coated | Free base, enteric coated | Hydrochloride salt, enteric coated | Placebo |
|---|---|---|---|---|
| Taste perversion | 5 | — | — | 1 |
| Skin odor abnormal | 3 | — | 2 | — |

TABLE 7-continued

| | Free base, non-enteric coated | Free base, enteric coated | Hydrochloride salt, enteric coated | Placebo |
|---|---|---|---|---|
| Urine abnormal | 2 | 1 | — | 1 |
| GI disorder NOS (foul smelling faeces) | 1 | 1 | — | — |
| Number of subjects with odor-related adverse events | 7 | 2 | 2 | 2 |
| Number of odor-related adverse events | 11 | 2 | 2 | 2 |

^1 of these subjects reported 2 different types of abnormal skin odor in the same session but is counted only once
— no events reported As can be clearly seen, the level of adverse events associated with the free base form of the compound was much lower when the compound was enterically coated.

COMPARATIVE EXAMPLE 7

Results of a study comparing adverse events seen with enterically coated tablets of hydrochloride salt and placebo.

A double-blind, 3-session, cross-over, placebo-controlled, repeat dose study in healthy subjects assessing the pharmacokinetics as well as frequency of odor-related adverse events reported with a range of doses of enteric coated formulation of 1-(N-(2-(Diethylamino)ethyl)-N-(4-(4-trifluoromethylphenyl)benzyl)aminocarbonylmethyl)-2-(4-fluorobenzyl)thio-5,6-trimethylenepyrimidin-4-one, hydrochloride salt was conducted. In this study, the frequency of odor-related adverse events was noted to be higher on active drug (hydrochloride salt) versus placebo as summarized in the table below:

TABLE 8

| Type of Odor-Related Adverse Event | Placebo | 20 mg (Hydrochloride salt, enteric coated) | 40 mg (Hydrochloride salt, enteric coated) | 60 mg (Hydrochloride salt, enteric coated) | 80 mg (Hydrochloride salt, enteric coated) |
|---|---|---|---|---|---|
| Taste perversion | — | 1 | — | 3 | 1 |
| Skin | — | 2 | 1 | 1 | 1 |
| Urine | 1 | 1 | 2 | 4 | 5 |
| Faeces | — | 2 | 1 | 1 | 2 |
| Flatulence | — | — | — | 1 | — |
| Eructation | 1 | — | 1 | — | 2 |
| Number of odor-related adverse events | 2 | 6 | 5 | 10 | 11 |
| Number of Subjects with odor-related adverse events | 2 | 3 | 3 | 6 | 5 |
| Number of Subjects Exposed | 27 | 12 | 12 | 12 | 13 |

— no events reported

EXAMPLE 8

Formulation Bioenhancement

Wet granulation is a standard process in pharmaceutical manufacturing.

1-(N-(2-(Diethylamino)ethyl)-N-(4-(4-trifluoromethylphenyl)benzyl)aminocarbonylmethyl)-2-(4-fluorobenzyl)thio-5,6-trimethylenepyrimidin-4-one (called "active" in this example) is an amine, and therefore, in humans, is less soluble at typical intestinal pH (pH 6.8) than at typical stomach pH (1 to 4). Therefore its availability is likely to be diminished by the application of an enteric coat to the tablet which will delay core dissolution until the tablet reaches the intestine. Alternative formulations have been developed, in which the particle size of active is reduced by milling. The result of this reduction is an increase in the surface area of active, which should lead to an increase in dissolution rate (after the destruction of the enteric coat). Over the period of time in which active is resident in the intestines, this increase in dissolution rate would be anticipated to lead to a higher availability.

Two size reduction techniques were investigated, viz. airjet milling (so-called "micronisation") and milling of a suspension of active with yttrium-zirconium beads (so-called "wet bead milling").

An in vitro three-armed study was performed on enteric-coated active tablets to test the hypothesis that particle size reduction increases dissolution rate. For each arm, an enteric-coated tablet containing active equivalent to 80 mg was placed in 500 mL simulated intestinal fluid (SIF, corresponding to the fasted state in humans, pH 6.8) held at 37° C. and stirred at 100 rpm in a USP2 dissolution apparatus. The three arms of the study differed only in the nature of the core: in the first arm, the core was manufactured by a wet granulation process with no particle size reduction; in the second arm, the core was manufactured by a wet granulation process from micronised active; in the third arm, the core was manufactured by a process involving the spray-drying of a wet bead milled suspension of active.

The concentration of active in solution is monitored by measuring its absorbance at a wavelength corresponding to its spectral maximum and using Beer's Law to calculate the fraction released.

The data obtained (shown in Table 9) confirm the aforementioned hypothesis:

TABLE 9

| | Fraction dissolved (% nominal content) | | |
|---|---|---|---|
| Time (Minutes) | No particle size reduction | Micronised | Wet bead milled |
| 0 | 0 | 0 | 0 |
| 5 | 0 | 0 | 0 |
| 10 | 0 | 0 | 0 |
| 15 | 0 | 0 | 0 |
| 20 | 1 | 3 | 1 |
| 25 | 3 | 11 | 3 |
| 30 | 6 | 20 | 8 |
| 35 | 9 | 26 | 14 |
| 40 | 11 | 30 | 21 |

TABLE 9-continued

| | Fraction dissolved (% nominal content) | | |
| --- | --- | --- | --- |
| Time (Minutes) | No particle size reduction | Micronised | Wet bead milled |
| 45 | 13 | 33 | 30 |
| 50 | 14 | 36 | 38 |
| 55 | 15 | 39 | 47 |
| 60 | 16 | 41 | 57 |
| 65 | 17 | 43 | 66 |
| 70 | 18 | 44 | 71 |
| 75 | 19 | 46 | 74 |
| 80 | 20 | 48 | 76 |
| 85 | 21 | 49 | 77 |
| 90 | 22 | 50 | 79 |
| 95 | 22 | 51 | 79 |
| 100 | 23 | 52 | 80 |
| 105 | 24 | 52 | 80 |
| 110 | 24 | 53 | 81 |
| 115 | 25 | 54 | 81 |
| 120 | 25 | 55 | 82 |

The invention claimed is:

1. A pharmaceutical formulation comprising a core which includes a pharmaceutically active ingredient which is 1-(N-(2-(diethylamino)ethyl)-N-(4-(4-trifluoromethylphenyl)benzyl)aminocarbonylmethyl)-2-(4-fluorobenzyl)thio-5,6-trimethylenepyrimidin-4-one and a casing which comprises an enteric polymer.

2. A pharmaceutical formulation according to claim 1 wherein said core further comprises a disintegrant.

3. A pharmaceutical formulation according to claim 2 wherein said disintegrant is croscarmellose sodium.

4. A pharmaceutical formulation according to claim 1 wherein said core further comprises a diluent.

5. A pharmaceutical formulation according to claim 4 wherein said diluent is lactose.

6. A pharmaceutical formulation according to claim 1 wherein said core further comprises a binder.

7. A pharmaceutical formulation according to claim 6 wherein said binder is hydroxypropylmethyl cellulose.

8. A pharmaceutical formulation according to claim 1 wherein said core comprises microcrystalline cellulose.

9. A pharmaceutical formulation according to claim 1 wherein said enteric polymer is an Eudragit® enteric polymer which is a methyl acrylate methacrylic acid copolymer.

10. A pharmaceutical formulation according to claim 1 wherein said casing further comprises an anti tack agent.

11. A pharmaceutical formulation according to claim 1 wherein said casing further comprises a surfactant.

12. A pharmaceutical formulation according to claim 1 wherein said active ingredient is micronised.

13. A process for making a pharmaceutical formulation according to claim 1 comprising wet bead milling.

14. A pharmaceutical formulation according to claim 5 wherein said diluent is anhydrous lactose, lactose monohydrate or a mixture thereof.

15. A pharmaceutical formulation according to claim 9 wherein said casing further comprises a plasticizer.

16. A pharmaceutical formulation according to claim 15 wherein said plasticizer is triethyl citrate.

17. A pharmaceutical formulation according to claim 1 further comprising a seal coat between said core and said casing.

18. A pharmaceutical formulation comprising:
(i) a core which comprises:
a pharmaceutically active ingredient, which is 1-(N-(2-(diethylamino)ethyl)-N-(4-(4-trifluoromethylphenyl)benzyl(aminocarbonylmethyl)-2-(4-fluorobenzyl)thio-5,6-trimethylenepyrimidin-4-one,
a disintegrant which is croscarmellose sodium,
a diluent, which is anhydrous lactose, lactose monohydrate, or a mixture thereof,
a binder, which is hydroxypropylmethyl cellulose,
microcrystalline cellulose, and
a lubricant; and
(ii) a casing which comprises an enteric polymer, an anti-tack agent, and a surfactant.

19. The formulation of claim 18 wherein the lubricant is magnesium stearate.

20. The formulation of claim 18 wherein the anti-tack agent is glyceryl monostearate and the surfactant is polysorbate 80.

21. A pharmaceutical formulation according to claim 18 wherein said casing further comprises a plasticizer.

22. A pharmaceutical formulation according to claim 21 wherein said plasticizer is triethyl citrate.

23. The formulation of claim 18 further comprising a seal coat between said core and said casing.

24. The formulation of claim 18 wherein the enteric polymer is a methacrylic acid copolymer.

25. The formulation of claim 1 where the enteric polymer is a methacrylic acid copolymer.

* * * * *